(12) United States Patent
Stuebinger

(10) Patent No.: US 10,537,408 B2
(45) Date of Patent: Jan. 21, 2020

(54) DENTAL IMPLANT

(71) Applicants: UNIVERSITAET BASEL, Basel (CH); UNIVERSITAET ZUERICH, Zurich (CH)

(72) Inventor: Stefan Bernd Stuebinger, Binningen (CH)

(73) Assignees: UNIVERSITAET BASEL, Basel (CH); UNIVERSITAET ZUERICH, Zurich (CH)

( * ) Notice: Subject to any disclaimer, the term of this patent is extended or adjusted under 35 U.S.C. 154(b) by 0 days.

(21) Appl. No.: 15/557,107

(22) PCT Filed: Mar. 3, 2016

(86) PCT No.: PCT/EP2016/054561
§ 371 (c)(1),
(2) Date: Sep. 10, 2017

(87) PCT Pub. No.: WO2016/142270
PCT Pub. Date: Sep. 15, 2016

(65) Prior Publication Data
US 2018/0042702 A1    Feb. 15, 2018

(30) Foreign Application Priority Data

Mar. 11, 2015  (DE) .................. 10 2015 103 544

(51) Int. Cl.
*A61C 8/00*   (2006.01)
*A61C 1/00*   (2006.01)
(Continued)

(52) U.S. Cl.
CPC .......... *A61C 8/0037* (2013.01); *A61C 1/0046* (2013.01); *A61C 3/03* (2013.01);
(Continued)

(58) Field of Classification Search
CPC ... A61C 8/0037; A61C 8/0006; A61C 8/0075; A61C 8/0089; A61C 8/0074;
(Continued)

(56) References Cited

U.S. PATENT DOCUMENTS 5,176,709 A * 1/1993 Branemark ........... A61F 2/3662
606/62
D356,868 S * 3/1995 Broberg ...................... D24/156
(Continued)

FOREIGN PATENT DOCUMENTS

CA        2549253      12/2007
DE     102005058496    6/2007
(Continued)

OTHER PUBLICATIONS

Office Action dated Apr. 12, 2019 in related/corresponding EP Application No. 16 707 488.9.

*Primary Examiner* — Matthew M Nelson
(74) *Attorney, Agent, or Firm* — Patent Portfolio Builders PLLC

(57) ABSTRACT

A dental implant includes an anchoring region (12) for anchoring in a bone, which preferably includes a thread (14) for screwing in the bone, and a fastening region (22) for attaching a supra-construction, wherein an abutment region (16) adjoins the anchoring region (12), the abutment region (16) having a guide structure with a plurality of outwardly projecting ridges (18) provided thereon, and preferably, grooves (20) being formed between the ridges (20). The guide structure of the anchoring region (12) allows a better osseointegration and counteracts peri-implant bone loss.

20 Claims, 6 Drawing Sheets

(51) Int. Cl.
*A61C 3/03* (2006.01)
*A61C 8/02* (2006.01)

(52) U.S. Cl.
CPC .......... *A61C 8/0006* (2013.01); *A61C 8/0022* (2013.01); *A61C 8/0066* (2013.01); *A61C 8/0074* (2013.01); *A61C 8/0075* (2013.01); *A61C 8/0089* (2013.01); *A61C 2008/0046* (2013.01)

(58) Field of Classification Search
CPC ... A61C 8/0066; A61C 8/0022; A61C 1/0046; A61C 3/03; A61C 2008/0046
USPC .................................................. 433/172–176
See application file for complete search history.

(56) References Cited

U.S. PATENT DOCUMENTS

| | | | | |
|---|---|---|---|---|
| 5,975,903 | A | | 11/1999 | Shoher et al. |
| 6,315,564 | B1 | * | 11/2001 | Levisman ............ A61C 8/0022 |
| | | | | 433/174 |
| 6,386,877 | B1 | * | 5/2002 | Sutter ................... A61C 8/0018 |
| | | | | 433/173 |
| 6,854,972 | B1 | * | 2/2005 | Elian .................... A61C 8/0006 |
| | | | | 433/173 |
| RE42,391 | E | * | 5/2011 | Wohrle ................ A61C 8/0012 |
| | | | | 433/173 |
| 2006/0194169 | A1 | * | 8/2006 | Chung ................. A61C 8/0018 |
| | | | | 433/173 |
| 2007/0099152 | A1 | * | 5/2007 | Busch .................. A61C 8/0001 |
| | | | | 433/173 |
| 2008/0085491 | A1 | * | 4/2008 | Ho ....................... A61C 8/0018 |
| | | | | 433/173 |
| 2011/0200969 | A1 | * | 8/2011 | Schroering .......... A61C 8/0018 |
| | | | | 433/174 |
| 2013/0011811 | A1 | * | 1/2013 | Gourlaouen-Preissler ................. |
| | | | | A61C 8/0012 |
| | | | | 433/173 |
| 2013/0273499 | A1 | * | 10/2013 | Hansson .............. A61C 8/0018 |
| | | | | 433/174 |
| 2014/0329201 | A1 | * | 11/2014 | Cottrell ................ A61C 8/0077 |
| | | | | 433/174 |
| 2015/0099239 | A1 | * | 4/2015 | Gourlaouen-Preissler ................. |
| | | | | A61C 8/0024 |
| | | | | 433/174 |
| 2015/0099240 | A1 | * | 4/2015 | Hansson .............. A61C 8/0018 |
| | | | | 433/174 |
| 2015/0190214 | A1 | * | 7/2015 | Dosta ................... A61C 8/0012 |
| | | | | 433/174 |

FOREIGN PATENT DOCUMENTS

| | | |
|---|---|---|
| EP | 2656813 | 10/2013 |
| EP | 2674127 | 12/2013 |
| WO | WO2011/064369 | 6/2011 |

* cited by examiner

DENTAL IMPLANT

CROSS-REFERENCE TO RELATED APPLICATIONS

This is the U.S. National Stage of International Application No. PCT/EP2016/054561 filed on Mar. 3, 2016, which was published in German under PCT Article 21(2), which in turn claims the benefit of German Patent Application No. 10 2015 103 544.8 filed on Mar. 11, 2015.

BACKGROUND AND SUMMARY OF THE INVENTION

The invention relates to an implant, in particular a dental implant, with an anchoring region (12) for anchoring in a bone, which preferably has a thread (14) for screwing into the bone, and with a fastening region (22) for fastening a supra-construction.

Dental Implants are in use in dentistry for decades.

Generally, dental implants are provided with an anchoring region having a threaded section, which is designed for screw-fastening in the bone. Further, a dental implant generally has a fastening region to which a supra-construction can be secured.

In one-piece implants, an extension (also referred to as an abutment) is provided, which protrudes from the anchoring region and to which supra-constructions can be attached. In the case of two-piece implants, a specifically designed recess is provided, to which an abutment can be fastened by screws or through form-fit.

Further, there are various constructions in which an additional thread is provided at the upper end of the anchoring region, which is finer than the thread in the lower region (Specifically, compare EP 2 656 813 A1, DE 10 2012 105 873 A1, WO 2014/091345 A2, WO 2003/015654 A1), or, which is coarser than the thread in the lower part of the anchoring region (Ep 1 764 060 A1).

According to WO 2003/015654 A1, at the upper end of the anchoring region, which is provided with a self-tapping thread, a fine-thread section is provided, which is preferably also slightly conical.

Through the fine thread section, the problem of bone resorption can be mitigated.

Several factors play a role in the long-term stability of implants. A sufficient osseointegration should be improved by a specific microstructure of the outer surface of the implant, wherein a semi-rough surface, produced by, for example, sandblasting, is advantageous. Even if the implant is initially well osseointegrated, there is often a noticeable pre-implant bone loss in course of time, due to which the long-term stability of the implant is impaired.

To this end, there have been on convincing approaches.

Addressing the current background, the invention is based on the objective of disclosing an implant which results in improved osseointegration, and which leads to minimum pre-implant bone loss.

The problem is solved by an implant, specifically a dental implant with an anchoring region for anchoring in a bone, which preferably has a thread for screwing into the bone, and with a fastening region for fastening a supra-construction, wherein an abutment region adjoining the anchoring region is provided, which has a guide structure with multiple outwardly projecting ridges on its outer surface.

The objective of the invention would be achieved in this manner.

It has been shown that the guide structure in the abutment region, with multiple outwardly projecting ridges, improves the osseointegration on one hand, reduces the pre-implant bone loss on the other end. The guide structure allows the bone tissue to grow or accumulates along the abutment region. To ensure a continuous bone accumulation, a broad area of bone is required. For this, the guide structure provides the necessary prerequisites.

According to another embodiment of the invention, a respective groove is formed between adjoining ridges.

According to an embodiment, the ridges extend at an angle to the longitudinal axis of the implant, which lies between 0° and 80°, preferably between 10° and 70°, more preferably between 20° and 60°, particularly preferably 35° and 55°.

This implies that the ridges can extend parallel to the longitudinal axis of the implant, or at a large or small angle to the longitudinal axis.

In contrast to the threaded structures known in the prior-art, the currently disclosed guide structure is not a thread. Threads cited in the prior-art are single-start threads with self-locking. Even if the guide structure in accordance with the invention would be interpreted as a multi-start thread, it differentiates itself from the threads known in the prior-art due to its multi-start feature. Additionally, in contrast to the threads in the prior-art, the self-locking feature is absent.

Self-locking does not require a considerably large pitch angle. The ridges of the guide structure can extend deviating from a path parallel to the longitudinal axis of the implant (i.e., at an angle of 0° to the longitudinal axis of the implant) angle at a maximum of 80° to the longitudinal axis of the implant, but significantly lower, with a maximum of 70° or 60°, making self-locking not possible.

In a further embodiment of the current invention, at least six, preferably at least ten, more preferably about 12 to 40 ridges are arranged along the outer surface of the abutment region, at regular or even intervals with respect to one another.

In contrast to a multi-start thread structure, the guide structure of the abutment region is provided with at least six or more ridges.

According to a further embodiment of the invention, the ridges extend helically or spirally along the outer surface of the abutment region.

In this manner, the ridges extend without interruption along the outer surface of the abutment region.

Further, the ridges can be inclined in a similar direction as a thread within the anchoring region, opposite to the longitudinal axis of the implant. Basically, an inclination in a reverse direction is also possible.

According to a further embodiment of the invention, in a planar development of the abutment region, the ridges extend convexly from the anchoring region, towards the end of the abutment region (coronal end) located distal to the anchoring region.

In such an embodiment, too, an augmentation can be secured through a screw movement, over the abutment region.

In accordance with another embodiment of the invention, the abutment region has a convex or a conical outer contour.

Such an embodiment has an advantage that only a linear or an interrupted linear contact region to the bone is provided, due to which the accumulation of the bone can be facilitated.

In a modification to the above-mentioned uninterrupted structure of the ridges, these ridges can also be interrupted.

According to a further modification of the invention, the ridges are formed from a series of projections arranged along a line.

The osseointegration hereby can be further improved, since an overall improved implantation of the bone structure can be achieved and locally elevated surface pressures are diminished.

According to a further modification of the invention, a first sequence of ridges extends parallel to one another along the abutment region, around the entire outer circumference, which is adjoined by a second sequence of ridges also extending parallel to one another along the entire outer circumference of the abutment region, where the second sequence of ridges is aligned or staggered to the first sequence of ridges.

According to a further embodiment of the invention, individual ridges are arranged at an offset relative to one another along the outer circumference, though arranged parallel to one another.

In a further modification of the invention, individual interrupted ridges are arranged between adjacent uninterrupted ridges.

In a further modification of the invention the individual ridges are arranged at an angle to one another in a regular pattern along the outer surface.

All of the embodiments mentioned herein are adapted to support improved osseointegration and reduce the peri-implant bone loss.

According to a further embodiment of the invention, the abutment region is provided to protrude from a borehole in the bones.

In this manner, the bone can attach itself well to the implant, in the abutment region adjacently adjoining the anchoring region, outside the screwed region, the screwed region being formed by the thread of the anchoring region.

According to a further embodiment of the invention, the abutment region is provided for anchoring an augmentation.

The augmentation can be arranged around the abutment region, or according to its structure, can be fixed to a certain manner.

The attachment of the augmentation to the abutment region is, therefore, advantageous when the bone strength is no longer sufficient to accommodate the minimum length of the implant, which is approximately 8 to 12 mm. Further, the abutment region is optimally suited and adapted to ensure safe osseointegration of the augmentation.

According to a further embodiment of the invention, the grooves exhibit a depth lower than the starts of a thread at the anchoring region.

It has been shown that a relatively small depth of the grooves is particularly advantageous for favorable osseointegration.

According to a further embodiment of the invention, the outer circumference at the anchoring region is greater than or equal to the outer circumference at the abutment region.

In this manner, when the implant is screwed in by means of the thread provided at its anchoring region, it is avoided that the abutment region also cuts into the bone. In this way, an optimal osseointegration at the abutment region is accomplished.

The implant in accordance with the invention can principally be designed either as a one-piece or a multi-piece implant. When it is designed as a double-piece implant, the fastening region preferably has a recess with fastening element for fastening an abutment.

Herein, an internal thread or at least one form-fitting element can be provided in the recess, for fastening an abutment.

In this case, the recess preferably extends outwardly from one end of the abutment region into the abutment region.

On the other hand, if the implant is designed as a one-piece implant, the fastening region protrudes outwards from the abutment region, and is designed as one-piece with the abutment region and the anchoring region.

Stated otherwise, the fastening region is designed as an abutment, which protrudes outwardly from the abutment region.

The implant preferably consists of ceramic, in particular of a zirconium oxide ceramic.

It has been found that surfaces with a particularly good osseointegration can hereby be provided. Also, such a material selection is particularly suitable for reconstructions in the anterior tooth area, as the color of the ceramic, such as zirconium oxide ceramic, strongly matches the natural tooth color.

In an alternative embodiment, the implant consists of a metallic material/alloy, in particular a titanium alloy. The implant may also consist of various alloys or gradient materials. Further, it is also possible to manufacture in 3D-printing from metal or ceramic.

This yields very good mechanical stability and ease of manufacturing.

According to a further embodiment of the invention, the implant is roughened on its outer surface, in particular mechanically by means of a radiation treatment, chemically by means of an etching treatment, or thermally by means of a laser treatment or through plasma treatment.

Additionally, the implant can be a chemically activated on its outer surface, in particular by means of an etching treatment or by application of a substance having affinity to bones.

By means of such surface treatment, including the treatment of the outer surface of the anchoring region and the abutment region, a substantially improved osseointegration can be achieved.

According to a further embodiment of the invention, the anchoring region has a first length in axial direction and the abutment region has a second length in the axial direction, wherein the first length is at least as large as the second length.

Herein, the first length can also be larger than the second length.

Here, preferably the second length can be approximately between 3 to 10 mm, wherein the cumulative length of the anchoring region and the abutment region can be at most 15 mm.

Depending on the application, this is the optimal length for the abutment region.

Finally, the ridges can either have a flattened or rounded at their outer surface.

This also supports accumulation of the bone.

Further, the invention provides a method for implanting an implant, comprising the following steps:
  Producing a recess in the bone which is adapted for receiving the anchoring region, in particular by drilling, ultrasonic cutting or laser cutting;
  screwing the implant into the bore in such a way that the abutment region either terminates at the bone level or protrudes beyond the bone only by a small amount, preferably by about 0.5 mm to 2 mm.

This variant is particularly preferred when sufficient bone-substance is available and no reinforcement through an augmentation is required.

On the other hand, if a reinforcement through an augmentation is required, the implantation can occur in the following manner:

Forming a recess in the bone by drilling, ultrasonic cutting or laser cutting, the recess being adapted to receive the anchoring region;

Anchoring the implant into the bone in a manner that abutment region protrudes beyond the bone by a small amount, preferably by about 1 mm to 10 mm, more preferably by 3 mm. to 10 mm;

Securing an augmentation in the abutment region.

It is obvious that the features of the invention mentioned above can not only be used in the particular combination indicated but also in other combinations and variations without departing from the scope of the invention.

BRIEF DESCRIPTION OF THE DRAWINGS

Further features and advantages of the invention will emerge from the following description of preferred exemplary embodiments with reference to the drawing, wherein:

FIG. 8 provides yet another side-view of another embodiment of the implant, according to the invention;

DETAILED DESCRIPTION

Figure 1:
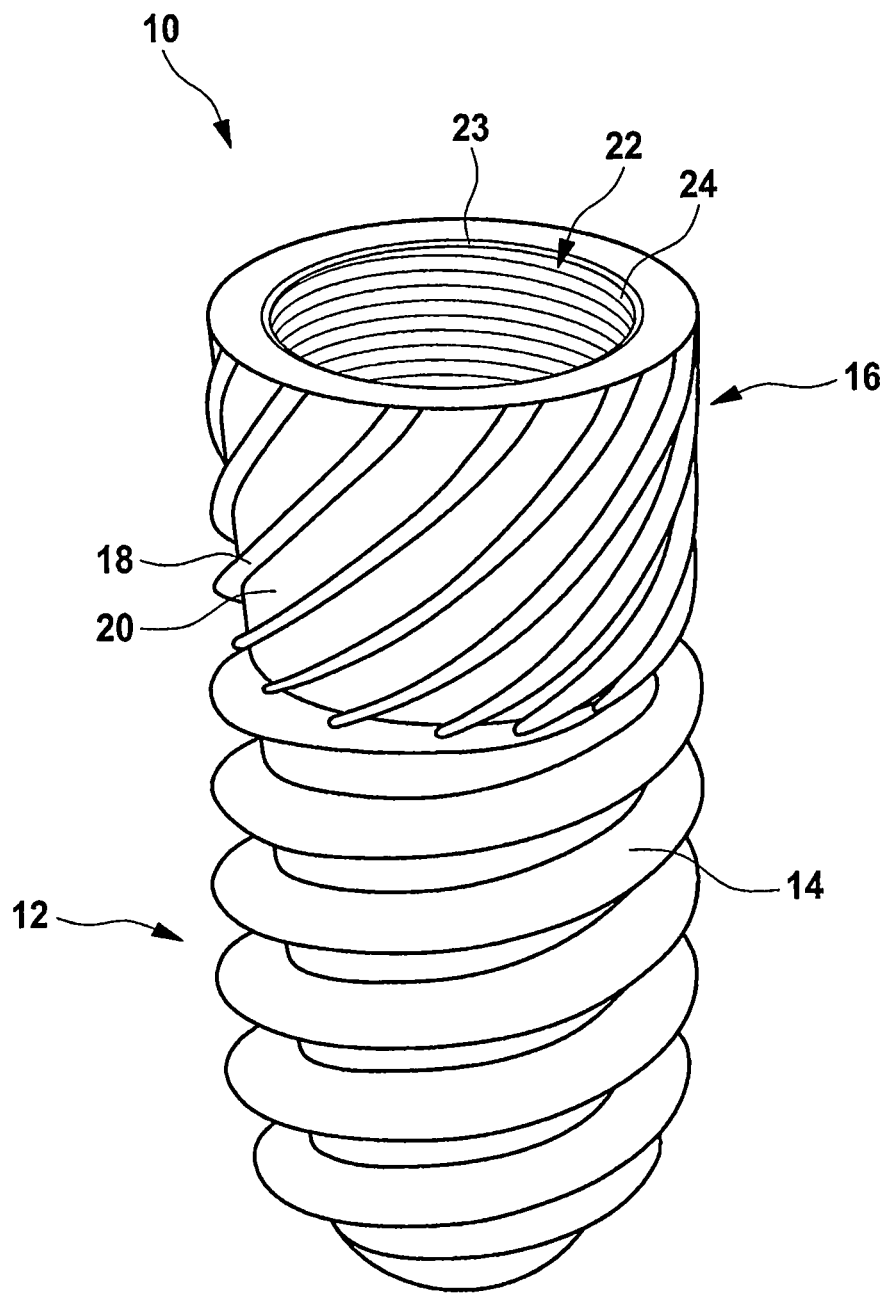
FIG. 1 is a perspective view of a first embodiment of an implant according to the invention.

FIG. 1 shows a perspective, enlarged view of a first embodiment of an implant in accordance with the present invention.

The implant 10 includes an anchoring region 12 with a self-tapping thread, which is provided for screwing the implant 10 into a suitable recess in the jawbone, the recess being usually produced by a bore, or by means of a laser, for example.

An additional region immediately adjoins the anchoring region 12, which is referred to as the abutment region 16 herein. The abutment region is meant for supporting a bone structure, to ensure good osseointegration, and simultaneously prevent a pre-implant bone loss.

Principally, the abutment region 16 has an outer diameter same or slightly smaller than the anchoring region 12. A guide structure is provided on the outer surface of the abutment region 16, which, in the illustrated case, has multiple outwardly projecting or protruding ridges 18, which are arranged parallel to one another and extend in a spiral form around the outer surface. A groove 20 is formed between respective adjacent ridges 18. In the currently depicted case, for example, there are 15 ridges arranged at regular intervals along the outer surface, in a helical manner. The depth of the grooves 20 on the abutment region 16 herein is considerably less than the depth of the thread 14 on the anchoring region 12.

The abutment region 16 is specially designed to facilitate and support the deposition of bone tissue. A screwing into the bone is achieved only with the anchoring region. To the contrary, the abutment region 16 can project outwards over the bore of the bone. Therefore, it can either be used to allow an accumulation of the bone tissue over its guide structure, or, can be used to attach an augmentation, through which an insufficient bone depth is compensated.

It has been shown that a particularly good osseointegration is ensured by the grooves 20 of small depth. Press-fit in the area of the abutment region 16 is avoided. This results in a significantly better pressure distribution relative to the adjacent bone, compared to the case with the thread in the anchoring region 12. The ridges 18 on the abutment region 16 do not form a thread, as is already known with some conventional implants. Even if one considers the anchoring region 12 with its ridges 18 as a multi-pass thread, it should be noted that in this case a large number of threads would be present, 15 in the current example, which is not known in the prior art.

Figure 4:
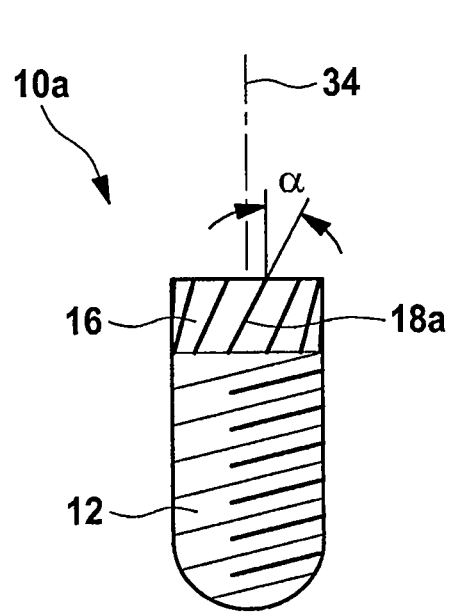
FIG. 4 is a simplified side-view of a further embodiment of the implant in accordance with the invention.

Additionally, the angle α between the longitudinal axis 34 of the implant and the ridges 18 is so small that no self-locking occurs (compare FIG. 4).

The implant 10 further has a fastening region 22, provided for receiving an abutment (not shown). In the implant 10 according to FIG. 1, the fastening region 22 has a recess 23, which extends from one end face of the abutment region 16 into the abutment region. An internal thread 24 is provided on the inner surface of the recess 23, which serves to screw an abutment. It is understood that instead of an internal thread 24, suitable form-fitting elements can also be provided in order to fasten an abutment, by producing a form-fit during screwing in, as is known in numerous embodiments in the prior art.

The implant may consist of metal or ceramic, for example zirconium oxide or of a titanic alloy. The outer surface of the implant is preferably suitably roughened, for example through a radiation treatment using corundum, or is chemically treated by means of an etching, for example, in order to achieve a surface particularly having an affinity to bones.

Figure 2:
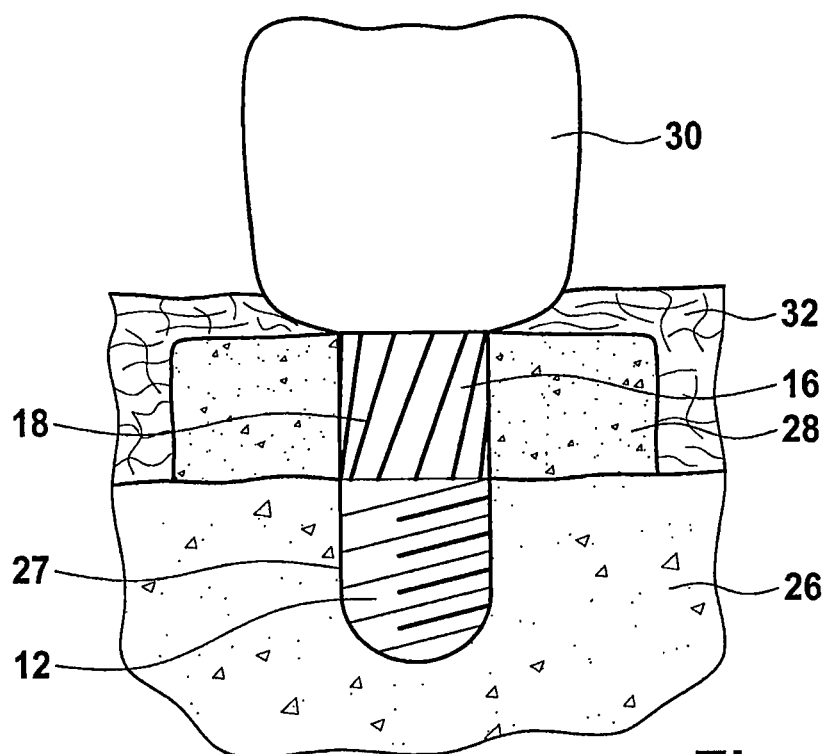
FIG. 2 depicts a first possibility of integration of the implant to a jaw bone with an additionally applied augmentation and a supra-construction.

FIG. 2 depicts a possible application area of the implant 10 on a jawbone.

A bore 27 has been inserted into the jawbone 26, into which the implant 10 is screwed by means the thread 14 on the anchoring region 12. The abutment region 16 projects outwards from the bone 26. An augmentation 28 was attached directly adjacent to the abutment region 16, which can be supported, when appropriate, through a certain screw movement when being placed on the ridges 18. A supra-construction 30 in the form of a crown is applied on the abutment region 16, which can occur by, for example, with the interposition of an abutment in accordance with the embodiment depicted in FIG. 1, when the implant is built as a two-piece implant.

Figure 3:
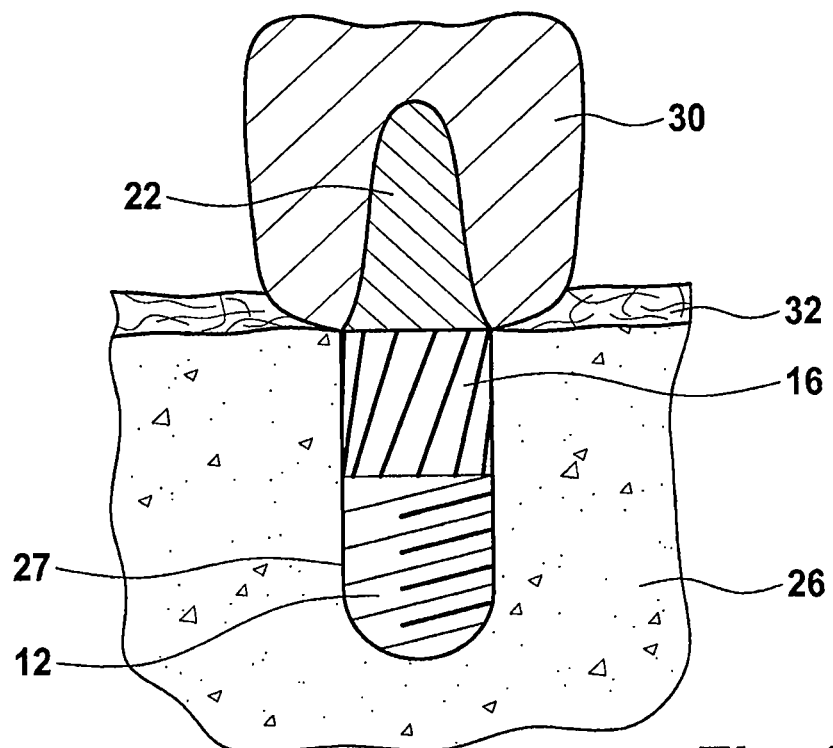
FIG. 3 depicts a second possibility of integration of the implant in the jaw, without additional augmentation.

Alternatively, the implant can also be designed as a one-piece implant, wherein the fastening region 22 is formed as a single-piece along with the abutment region 16 and the anchoring region 12, as shown in FIG. 3. In such a case, the fastening region 22 forms the abutment itself, to which a crown or any other supra-structure 30, as shown, can be attached.

No augmentation is used in the embodiment according to FIG. 3, since the depth of the bone herein is sufficient to directly receive the implant. The gingiva immediately adjoins the bone 26 and reaches the outer end of the abutment region 16 on successful implantation.

The abutment region 16 improves the level of osseointegration and also inhibits pre-implant bone loss.

The length of the bore 27 in FIG. 3 is dimensioned in such a manner that the entire implant 10, including its anchoring region 12 and the abutment region 16, is completely accommodated within the bore 27, and only the fastening region 22 of the implant 10 protrudes/extends outwards from the bone 26. Therefore, the length of the bore 27 is designed in such a way that the implant 10 terminates at the end of the abutment region 16, approximately at the level of the bone 26 ("Bone-Level"), or maximally by a small amount above the bone level, which may be 0.5 to 1 millimeters.

The diameter of the implant 10 in the abutment region 16 is, therefore, preferably, slightly smaller than its diameter in the anchoring region 12, so that when the implant 10 is screwed-in with its thread 14 in the bore 27, between the abutment region 16 and the bone 26, there is no or substantially minimal surface pressure. Preferably, a small gap remains so that the bone can grow and accumulate along the guide structure of the abutment region 16, towards the implant 10.

Different variants of the implant according to the invention are explained below with reference to FIG. 4 to FIG. 10.

Herein, corresponding reference numerals are used for corresponding elements.

FIG. 4 depicts an implant 10a according to the invention, wherein the abutment region 16 is slightly smaller than in the embodiments described above. Such a smaller region is specifically advantageous in cases where the implant 10a is to be used directly for implantation, without an additional augmentation. In this case, the implant 10a is preferably screwed into a drill hole in the jawbone in such a manner that the abutment region 16 protrudes by a small amount of about 0.5 to 2 mm. The bore can also be designed in such a way that the abutment region 16 still partially protrudes into the borehole, and either does not protrude at all, or, protrudes by a very small amount over the edge of the bone 26.

Figure 5:
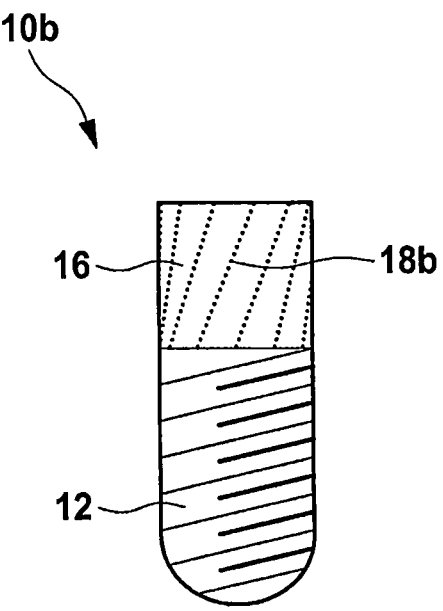
FIG. 5 is a side-view of a further modification of the implant, in accordance with the invention.

In FIG. 5, a side view of an implant in accordance with another embodiment of the invention is depicted and is designated overall by numeral 10b. In this case, instead of uninterrupted ridges in the abutment region 16, ridges 18b are provided, which are formed by a series of projections arranged along a line. The ridges 18b formed by the as individual projections, are arranged parallel to one another, similar to the case in the embodiments above.

Figure 6:
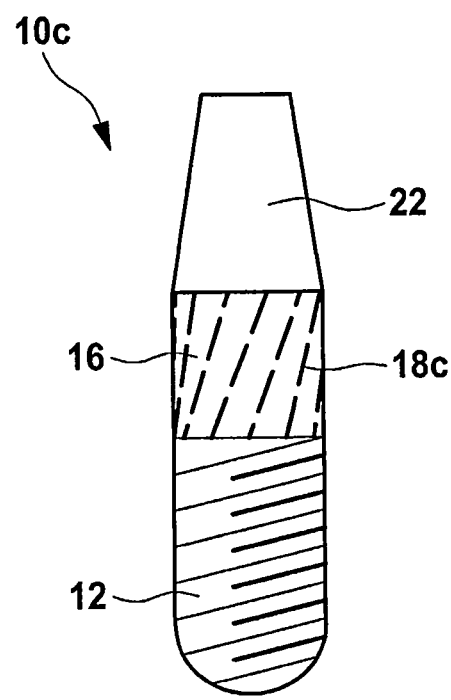
FIG. 6 is a side-view of another embodiment of an implant in accordance with the invention.

FIG. 6 depicts another modification of an implant according to the invention, which is indicated by numeral 10c. Here, the fastening region 22 adjoins the body section 18b, and is designed as an outwardly protruding abutment. This is, therefore, an implant designed as one-piece.

In a modification to the previously described embodiments, the abutment region 16 has a series of interrupted ridges 18c, which each extend over the entire length of the abutment region 16, and parallel to each other at uniform intervals over the entire outer circumference of the abutment region 16.

Figures 7, 8, 9:
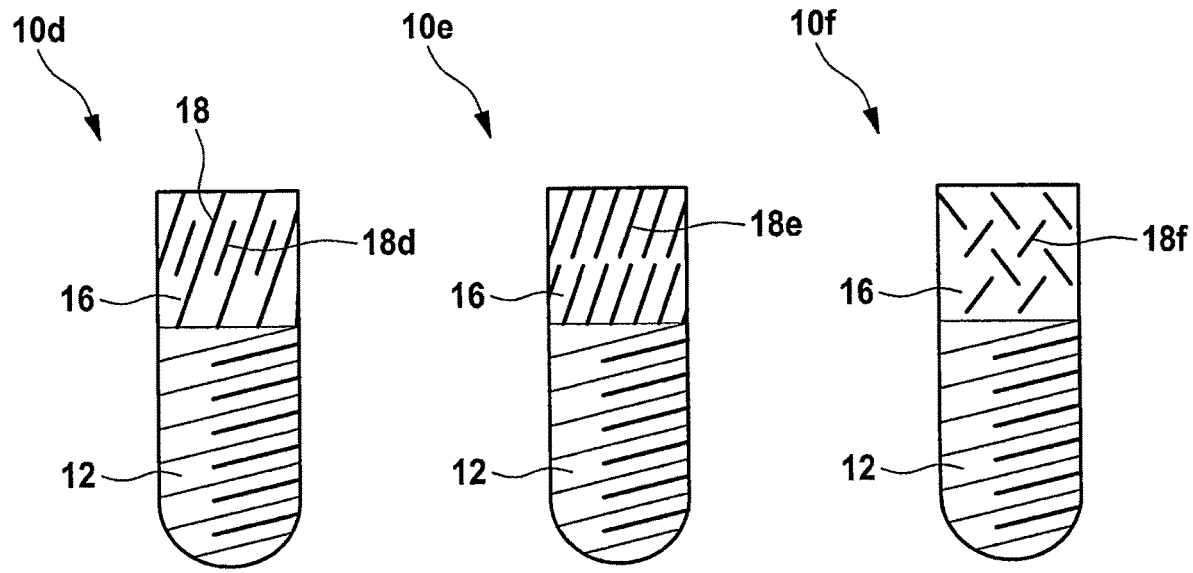
FIG. 7 is a side-view of a further embodiment of the implant in accordance with the invention.
FIG. 8 is a side-view of another embodiment of the implant, according to the invention.

FIG. 7 illustrates a further modification of an implant according to the invention, denoted generally by numeral 10d. In the shown embodiment, the abutment region 16 includes a sequence of uninterrupted ridges 18, wherein shorter ridges 18d are arranged between the adjacent ridges 18, which extend likewise parallel to the remaining ridges 18. The shorter ridges 18d also extend likewise parallel to ridges 18.

FIG. 8 depicts another modification of an implant according to the invention, indicated altogether by numeral 10e. Herein, two sequences of roughly, equally sized ridges 18e are provided over the surface of the abutment region 16. A first sequence of ridges 18e extending parallel to one another is provided over a first half of the abutment region 16. Similarly, a second sequence of ridges 18e are arranged parallel to one another over a second half of the abutment region and can either be aligned with or at an offset to the first ridges 18e.

FIG. 9 finally illustrates a further embodiment of an implant in accordance with the present invention, indicated altogether by numeral 10f.

Herein, the abutment region 16 is provided with a number of ridges 18f over its surface, arranged in a regular pattern along the outer circumference, the ridges 18f being arranged at an angle to, and at an offset to one another.

Figure 10:
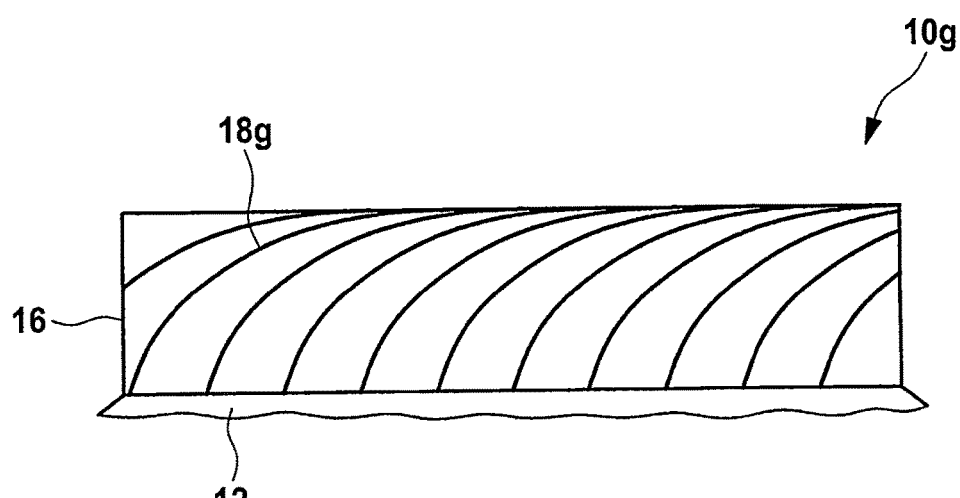
FIG. 10 is a further modification of an implant in accordance with the invention, wherein only the abutment region is depicted in a planar development.

FIG. 10 shows a yet another modification of an implant in accordance with the present invention, designated altogether by numeral 10g. Herein, only a planar development of the abutment region 16 with the adjoining anchoring region 12 is shown in the form of an enlarged view. While in the embodiment shown in FIG. 1, the ridges 18 extend linearly in the development, or extend outwards from the anchoring region 12 in their inclination, towards the end of the abutment region 16, i.e., concave, the ridges 18g according to FIG. 10 are exactly reversed, i.e., convex, with respect to the end of the implant 10g located distal to the anchoring region 12. In such an embodiment, too, an augmentation can be attached via a screw movement to the abutment region 16.

Figure 11:
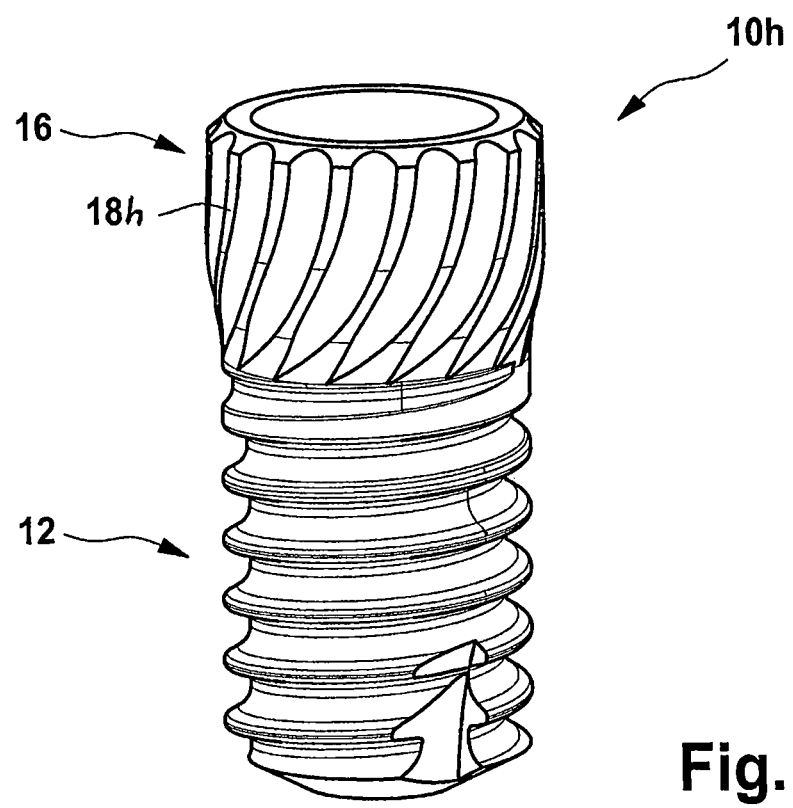
FIG. 11 is a perspective view of a further embodiment of an implant in accordance with the invention.
Figure 12:
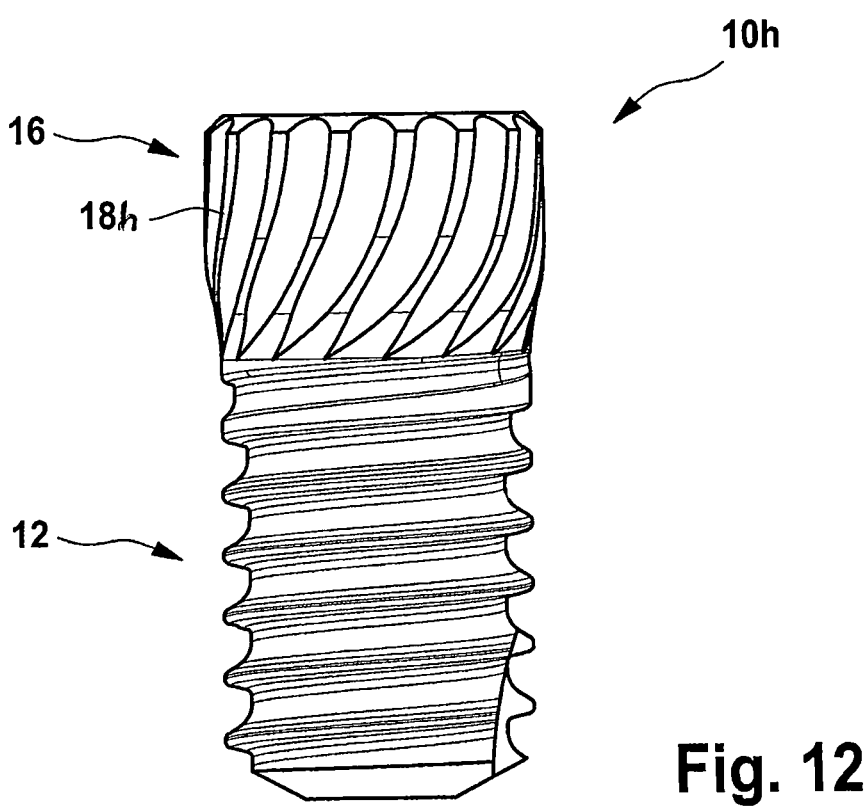
FIG. 12 is a side-view of the implant shown in FIG. 11.

FIG. 11 and FIG. 12 depict an embodiment of the implant, designated altogether by 10h, which is slightly different from the embodiment according to FIG. 1. Herein, the shape of the thread in the anchoring region 12 is slightly modified. The shape of the ridges 18 in the abutment region 16 is also slightly modified. In particular, the ridges 18h do not taper radially outwards, as is the case with customary threads, but have a flat outer surface.

This supports an improved osseointegration.

Figure 13:
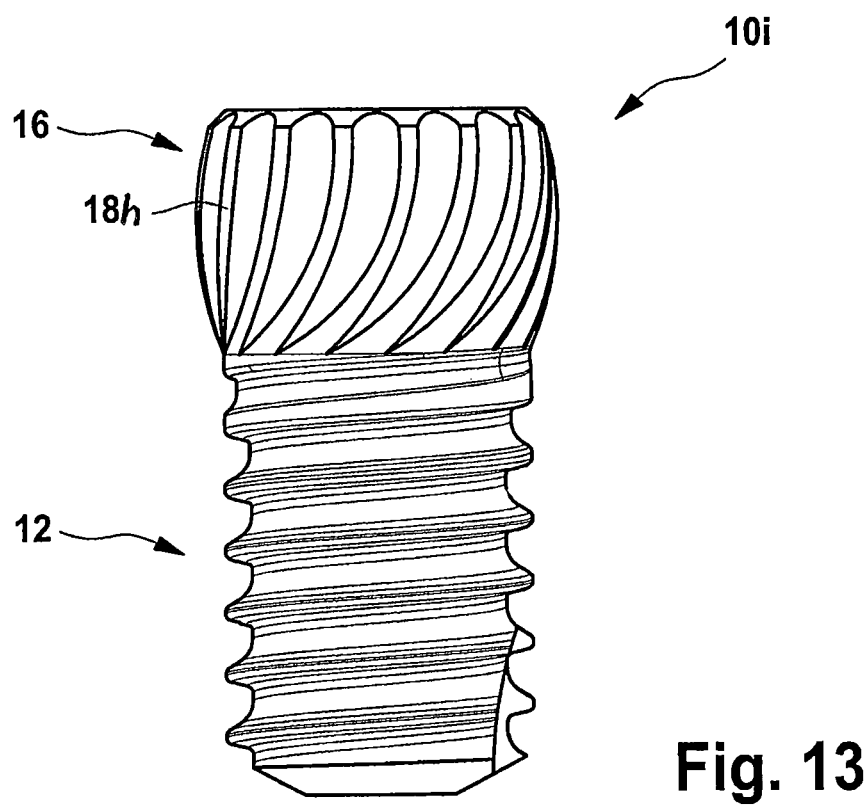
FIG. 13 is a side-view of a further modification of the implant depicted in FIG. 11.

FIG. 13 is a further modification of the implant according to FIGS. 11 and 12, which is designated altogether by numeral 10i. Herein, the abutment region 16 has a convex outer contour.

Figure 14:
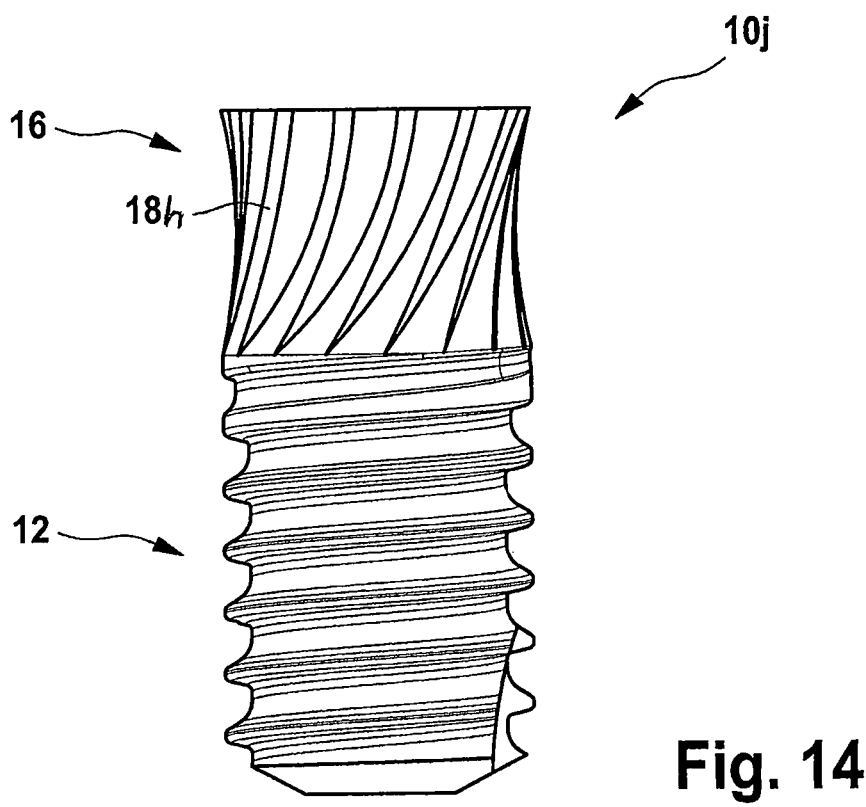
FIG. 14 is a side-view of yet another modification of the implant according to FIG. 11.

A reverse case of an implant having an abutment region 16 with concave contour is also conceivable, as shown by the implant 10j depicted in FIG. 14.

Due to the concave or convex outer contour, there is only a point or linear contact with the bone, with interruptions in the region of the grooves between the ridges 18.

Thus, the bone can easily accumulate to the surface in the abutment region 16.

Further modifications of the guide structure of the abutment region 16 are also conceivable.

The invention claimed is:

1. A dental implant comprising:
   an anchoring region for anchoring into a bone, the anchoring region having a thread for screwing into a bone;
   a fastening region for fastening a supra-construction; and
   an abutment region adjoining the anchoring region and forming a top surface of the dental implant, the abutment region having a guide structure with a plurality of outwardly projecting ridges provided on its outer surface and a groove formed between respective ones of the plurality of ridges,
   wherein the plurality of ridges include at least three ridges,
   wherein the abutment region has a top and a bottom and the grooves formed between the plurality of ridges extend from the top to the bottom of the abutment region, and
   wherein the plurality of ridges do not form a thread.

2. The dental implant of claim 1, wherein at least six ridges are arranged and extend along the outer surface of the abutment region, wherein the ridges are arranged at regular intervals to each other.

3. The dental implant of claim 1, wherein the ridges extend helically along the outer surface of the abutment region.

4. The dental implant of claim 1, wherein the ridges i) are inclined in the same direction as a thread on the anchoring region respective to the longitudinal axis of the implant, or ii) are inclined in the opposite direction as a thread on the anchoring region respective to the longitudinal axis of the implant.

5. The dental implant of claim 1, wherein the abutment region has a convex or a concave outer contour.

6. The dental implant of claim 1, wherein at least some of the ridges are interrupted.

7. The dental implant of claim 6, wherein the ridges are formed as a series of projections arranged along a line.

8. The dental implant of claim 6, wherein a first sequence of ridges is arranged parallel to one another along the entire outer circumference, along the abutment region, and a second sequence of ridges is arranged parallel to one another, along the entire circumference of the abutment region, wherein the second sequence of ridges aligns with, or is positioned at an offset to the first sequence of ridges.

9. The dental implant of claim 6, wherein individual ridges of said interrupted ridges are arranged between adjacent uninterrupted ridges.

10. The dental implant of claim 6, wherein the individual ridges are arranged in a regular pattern angular to one another along the outer circumference.

11. The dental implant of claim 1, wherein the grooves have a lower depth than the starts of a thread on the anchoring region.

12. The dental implant of claim 1, wherein the outer circumference of the anchoring region is larger than or equal to the outer circumference of the abutment region.

13. The dental implant of claim 1, wherein the fastening region has a recess, the recess having a fastening element for fastening an abutment.

14. The dental implant of claim 13, wherein an internal thread or at least a form-fitting element is provided in the recess, for fastening an abutment.

15. The dental implant of claim 1, wherein the fastening region projects outwards from the abutment region and is designed as a one-piece along with the abutment region and the anchoring region.

16. The dental implant of claim 1, wherein the ridges have a flattened outer surface.

17. The dental implant of claim 1, wherein the ridges extend without interruption between the top and bottom of the abutment region.

18. A method of implanting a dental implant, the method comprising:
   forming a recess in the bone, the recess being adapted to receive the anchoring region and being formed by drilling, ultrasonic cutting or laser cutting; and
   anchoring the implant in the recess in a manner that the abutment region aligns approximately with the bone level, or projects over the bone level by a small amount, the amount being a maximum of 0.5 millimeter to 2 millimeters, the dental implant comprising
   an anchoring region for anchoring into a bone, the anchoring region having a thread for screwing into a bone;
   a fastening region for fastening a supra-construction; and
   an abutment region adjoining the anchoring region and forming a top surface of the dental implant, the abutment region having a guide structure with a plurality of outwardly projecting ridges provided on its outer surface and a groove formed between respective ones of the plurality of ridges,
   wherein the plurality of ridges include at least three ridges,
   wherein the abutment region has a top and bottom and the grooves formed between the plurality of ridges extend from the top to the bottom of the abutment region, and
   wherein the plurality of ridges do not form a thread.

19. A dental implant comprising:
   an anchoring region for anchoring into a bone, the anchoring region having a thread for screwing into a bone;
   a fastening region for fastening a supra-construction; and
   an abutment region adjoining the anchoring region and forming a top surface of the dental implant, the abutment region having a guide structure with a plurality of outwardly projecting ridges provided on its outer surface and a groove formed between respective ones of the plurality of ridges,
   wherein the plurality of ridges include at least three ridges,
   wherein the abutment region has a top and bottom and the grooves formed between the plurality of ridges extend from the top to the bottom of the abutment region, and
   wherein in a planar development of the abutment region the ridges have a convex shape from the anchoring region towards the end of the abutment region located distal to the anchoring region, and
   wherein the plurality of ridges do not form a thread.

20. The dental implant of claim 19, wherein the ridges extend without interruption between the top and bottom of the abutment region.

* * * * *